(12) United States Patent
Russell et al.

(10) Patent No.: US 9,681,744 B2
(45) Date of Patent: Jun. 20, 2017

(54) LIGHT EMITTING ORAL CARE IMPLEMENT AND METHOD OF DETECTING PLAQUE

(71) Applicant: Colgate-Palmolive Company, New York, NY (US)

(72) Inventors: Bruce M. Russell, Howell, NJ (US); Robert A. Moskovich, East Brunswick, NJ (US); Michael Prencipe, West Windsor, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 0 days.

(21) Appl. No.: 15/086,639

(22) Filed: Mar. 31, 2016

(65) Prior Publication Data

US 2016/0278640 A1    Sep. 29, 2016

Related U.S. Application Data

(63) Continuation of application No. 13/012,604, filed on Jan. 24, 2011, now abandoned, which is a
(Continued)

(51) Int. Cl.
*A46B 15/00* (2006.01)
*A61B 5/00* (2006.01)
(Continued)

(52) U.S. Cl.
CPC ............ *A46B 15/0034* (2013.01); *A46B 9/04* (2013.01); *A46B 15/0002* (2013.01); *A46B 15/0036* (2013.01); *A61B 5/0071* (2013.01); *A61B 5/0088* (2013.01); *A61B 5/4547* (2013.01); *A61C 17/34* (2013.01); *A61C 19/066* (2013.01); *A46B 15/0044* (2013.01); *A46B 2200/1066* (2013.01); *A61C 19/004* (2013.01)

(58) Field of Classification Search
CPC ............ A46B 15/0034; A46B 15/0036; A46B 15/0016; A46B 2200/1066; A46B 15/0044; A61B 5/0088; A61B 5/0071
See application file for complete search history.

(56) References Cited

U.S. PATENT DOCUMENTS 3,261,978 A    7/1966    Brenman
3,309,274 A    3/1967    Herbert
(Continued)

FOREIGN PATENT DOCUMENTS

JP    09140454    6/1997
JP    2001114658    4/2001
(Continued)

*Primary Examiner* — Laura C Guidotti

(57) ABSTRACT

A toothbrush uses light to deliver an oral care benefit such as the detection of plaque or the whitening of teeth. In one embodiment, a toothpaste formulation contains ultraviolet brighteners as a whitening ingredient that has a whitening or bleaching effect when in contact with ultraviolet radiation. The activation of the brighteners may occur through the use of a toothbrush having a UV source. In yet another embodiment, a toothpaste formulation contains an oxidizing agent as a whitening ingredient, the activation of which occurs through the use of a toothbrush having a source of light energy which includes LEDs in the bristle field.

8 Claims, 3 Drawing Sheets

Related U.S. Application Data continuation of application No. 11/464,182, filed on Aug. 11, 2006, now abandoned, which is a continuation of application No. PCT/US2005/003506, filed on Jan. 28, 2005, which is a continuation of application No. 10/776,972, filed on Feb. 11, 2004, now abandoned, and a continuation of application No. 10/776,554, filed on Feb. 11, 2004, now abandoned, and a continuation of application No. 10/767,573, filed on Jan. 29, 2004, now abandoned.

(51) Int. Cl.
*A61C 17/34* (2006.01)
*A61C 19/06* (2006.01)
*A46B 9/04* (2006.01)
*A61C 13/15* (2006.01)

(56) References Cited

U.S. PATENT DOCUMENTS

| | | |
|---|---|---|
| 3,667,454 A | 6/1972 | Prince |
| 4,184,196 A | 1/1980 | Moret et al. |
| 4,517,172 A | 5/1985 | Southard |
| 4,590,061 A | 5/1986 | Southard |
| 4,661,070 A | 4/1987 | Friedman |
| 4,952,143 A | 8/1990 | Becker et al. |
| 5,032,178 A | 7/1991 | Cornell |
| 5,306,143 A | 4/1994 | Levy |
| 5,382,163 A | 1/1995 | Putnam |
| 5,625,916 A | 5/1997 | McDougall |
| 5,645,628 A | 7/1997 | Endo et al. |
| 5,713,738 A | 2/1998 | Yarborough |
| 5,894,620 A | 4/1999 | Polaert et al. |
| 6,024,562 A | 2/2000 | Hibst et al. |
| 6,026,828 A | 2/2000 | Altshuler et al. |
| 6,094,767 A | 8/2000 | Iimura |
| 6,162,055 A | 12/2000 | Montgomery et al. |
| D438,622 S | 3/2001 | Chang |
| 6,202,242 B1 | 3/2001 | Salmon et al. |
| 6,231,343 B1 | 5/2001 | Ishibashi et al. |
| 6,239,442 B1 | 5/2001 | Iimura |
| 6,254,388 B1 | 7/2001 | Yarborough |
| 6,318,996 B1 | 11/2001 | Melikechi et al. |
| 6,343,400 B1 | 2/2002 | Massholder et al. |
| 6,343,933 B1 | 2/2002 | Montgomery et al. |
| 6,416,319 B1 | 7/2002 | Cipolla |
| 6,485,300 B1 | 11/2002 | Muller et al. |
| 6,517,532 B1 | 2/2003 | Altshuler et al. |
| 6,616,451 B1 | 9/2003 | Rizolu et al. |
| 6,623,272 B2 | 9/2003 | Clemans |
| 6,675,425 B1 | 1/2004 | Iimura |
| 6,902,397 B2 | 6/2005 | Farrell et al. |
| 2001/0024777 A1 | 9/2001 | Azar et al. |
| 2002/0128635 A1 | 9/2002 | Altshuler et al. |
| 2002/0137001 A1 | 9/2002 | Cipolla et al. |
| 2003/0059738 A1 | 3/2003 | Neuberger |
| 2003/0104340 A1 | 6/2003 | Clemans et al. |
| 2003/0195494 A1 | 10/2003 | Altshuler et al. |
| 2004/0019990 A1 | 2/2004 | Farrell et al. |
| 2004/0053190 A1 | 3/2004 | Lin |
| 2004/0191729 A1 | 9/2004 | Altshuler et al. |
| 2004/0193235 A1 | 9/2004 | Altshuler et al. |
| 2004/0193236 A1 | 9/2004 | Altshuler et al. |
| 2004/0204745 A1 | 10/2004 | Altshuler et al. |
| 2004/0210276 A1 | 10/2004 | Altshuler et al. |
| 2005/0038418 A1 | 2/2005 | Altshuler et al. |
| 2005/0050658 A1 | 3/2005 | Chan et al. |
| 2005/0053895 A1* | 3/2005 | Pinyayev ............... A61C 17/22 433/29 |
| 2005/0107849 A1 | 5/2005 | Altshuler et al. |
| 2005/0170316 A1 | 8/2005 | Russell et al. |
| 2005/0172429 A1 | 8/2005 | Russell et al. |
| 2005/0175956 A1 | 8/2005 | Russell et al. |

FOREIGN PATENT DOCUMENTS

| | | |
|---|---|---|
| WO | WO9510243 | 4/1995 |
| WO | WO2004028948 | 4/2004 |
| WO | WO2005072642 | 8/2005 |

\* cited by examiner

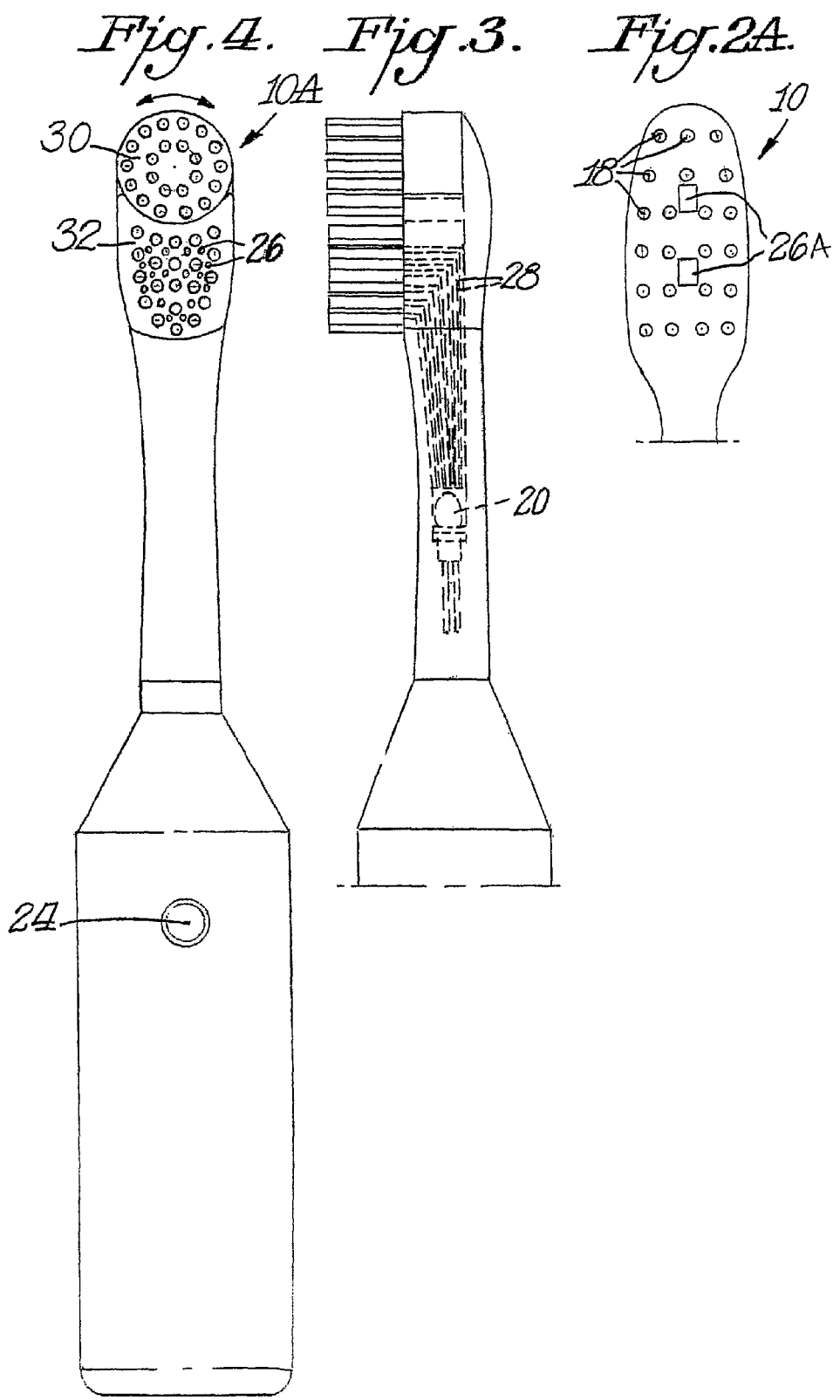

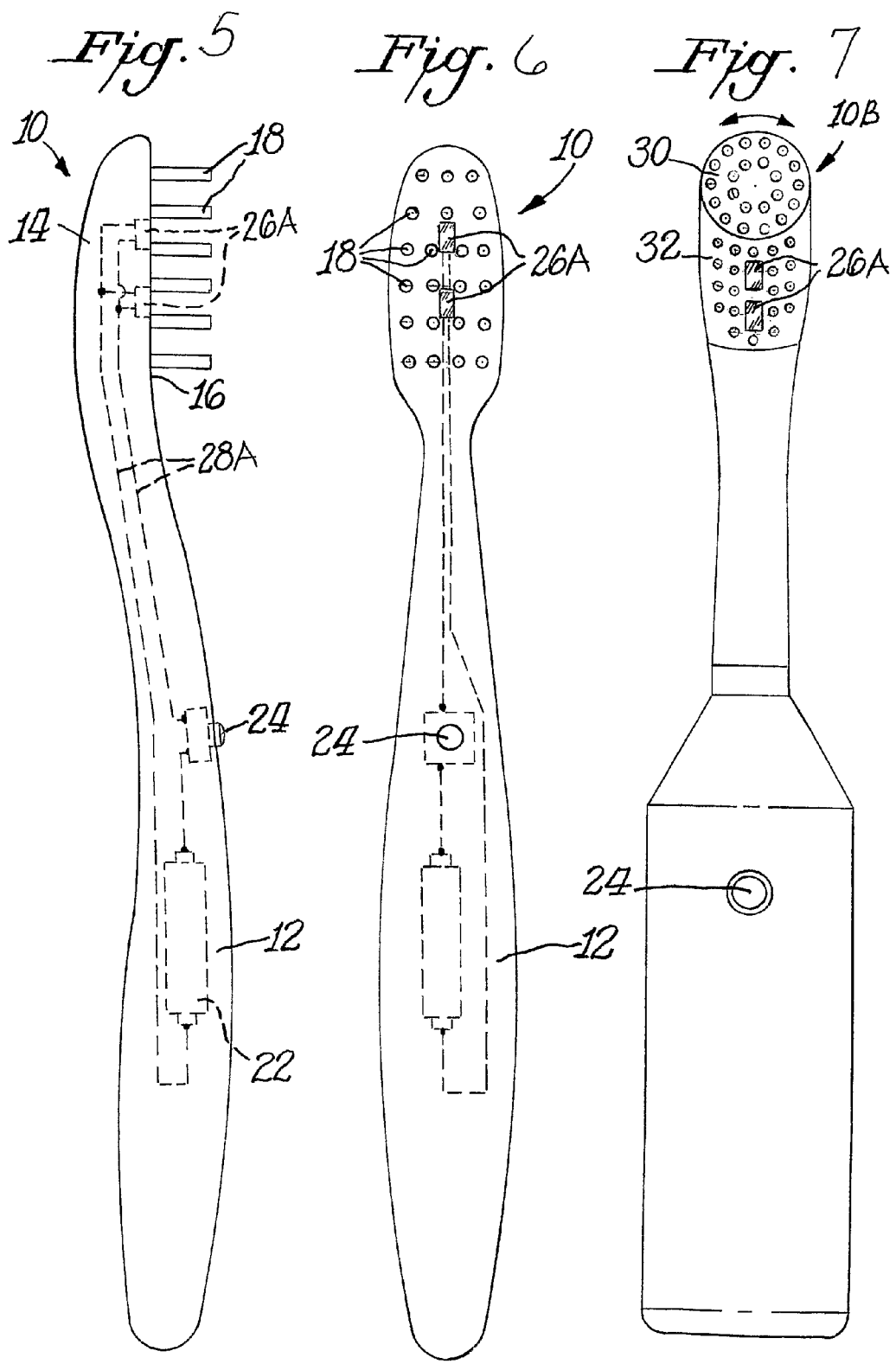

LIGHT EMITTING ORAL CARE IMPLEMENT AND METHOD OF DETECTING PLAQUE

CROSS-REFERENCE TO RELATED APPLICATIONS

The present application is a continuation of U.S. application Ser. No. 13/012,604, filed Jan. 24, 2011, which is a continuation of U.S. application Ser. No. 11/464,182, filed Aug. 11, 2006, which is a continuation of PCT Application No. PCT/US2005/003506, filed Jan. 28, 2005, which claims the benefit of priority to U.S. application Ser. No. 10/776,972, filed Feb. 11, 2004, U.S. application Ser. No. 10/776,554, filed Feb. 11, 2004, and U.S. application Ser. No. 10/767,573, filed Jan. 29, 2004, the entireties of which are incorporated herein by reference.

BACKGROUND

Various techniques have been used to deliver an oral care benefit to one's teeth. In some cases, techniques have been used attempting to detect the presence of plaque on one's teeth. Such techniques include, for example, the application of various compositions to the teeth which are intended to visually indicate the presence of plaque. It would be highly advantageous for a person brushing one's teeth to obtain feedback immediately upon brushing regarding the brushing effectiveness.

Various techniques have also been used for creating a whitening effect of a user's teeth. Current at home tooth whitening techniques require several days for the user to see the effect of the treatment and are generally considered to be inconvenient and in some cases difficult to use. It would be desirable to provide techniques which give a more immediate whitening effect so as to encourage the user to have a regular brushing program in addition to giving the satisfaction of whiter teeth.

A technique marketed by BriteSmile, Inc. involves providing a tooth whitening composition which includes an oxidizing compound which when applied to a stained tooth and exposed to actinic light is activated to facilitate tooth whitening. The light is provided by a device which has a generally crescent-shaped surface with spaced optical outputs located along the surface. In practice the device would be applied for an extended period of time. Examples of compositions and devices of BriteSmile, Inc. are found in U.S. Pat. Nos. 5,645,628, 5,713,738, 6,162,055, 6,254,388, 6,343,933, 6,416,319 and D438,622 and in published patent application US2002/0137001. Other U.S. patents dealing with the whitening of teeth are U.S. Pat. Nos. 4,661,070, 4,952,143 and 5,032,178. Typically, where lights have been used to activate the oxidizing agent such lights have been xenon lamps, flash lamps, mercury short arc lamps, metal halide lamps, tungsten halogen lamps, etc.

SUMMARY

In accordance with one embodiment of this invention, a dye is incorporated in a carrier. The dye has the characteristic of being able to attach itself to residual plaque on the tooth surface and also has the characteristic of becoming fluorescent in the presence of ultraviolet radiation. In a broad practice of this invention an ultraviolet light source is used for directing ultraviolet light against the teeth so that the fluorescent effect would be created and easily visible to the user to indicate the presence of residual plaque. In a preferred practice of this invention the ultraviolet light source is incorporated in a toothbrush. The carrier for the dye could be the toothpaste on the toothbrush cleaning head. Alternatively, the carrier could be some form of liquid such as an oral rinse or mouthwash or could be a gum or lozenge or polymer strip or any other common devices used for delivering oral health benefits.

In accordance with another embodiment of this invention, optical brighteners are incorporated in a carrier, such as toothpaste. The brighteners have the characteristic of being able to have a whitening or bleaching effect when coming into contact with ultraviolet radiation. The carrier would also include an adhering agent which would adhere to the teeth while the brighteners adhere to the adhering agent. As a result the brighteners remain on the outer surface of the teeth. In the broad practice of this embodiment, an ultraviolet light source is used for directing ultraviolet light against the teeth so that the whitening effect would be created and easily visible to the user. In a preferred practice of this embodiment, the ultraviolet light source is incorporated in a toothbrush. The carrier for the brightener is preferably the toothpaste on the toothbrush cleaning head.

In accordance with another embodiment of this invention, an oxidizing agent is provided which may be activated by light and/or heat energy in order to speed the chemical process of whitening stained teeth. The oxidizing agent is applied to the teeth preferably by toothpaste, although other forms of application may be used such as whitening gels, whitening strips or other such products. In the broad practice of this embodiment, an ultraviolet or infrared radiation source is used for directing radiation against the teeth so that the oxidizing agent would be activated. In a preferred practice of this embodiment, the radiation source is from LED devices incorporated in a toothbrush. The carrier for the oxidizing agent is preferably the toothpaste on the toothbrush cleaning head.

In accordance with yet another embodiment, the invention may be an oral care implement comprising: a handle; a head attached to said handle, said head having a front surface with cleaning elements extending outwardly therefrom; at least one light emitting diode located on said head to radiate light at a wavelength between 350-410 nm toward a user's teeth; and wherein said at least one light emitting diode is surface mounted on the head so as to not protrude beyond the front surface of the head.

In accordance with still another embodiment, the invention may be a method for detecting the presence of plaque on a user's teeth comprising: incorporating in a toothpaste a dye which has the characteristic of attaching to plaque and which has the characteristic of being fluorescent in the presence of ultraviolet (UV) light; applying the toothpaste to the user's teeth, the dye attaching to or being absorbed by plaque on the user's teeth; rinsing the user's mouth so that the only dye remaining in the user's mouth is the dye which is attached to plaque on the user's teeth; radiating UV light from a UV light source toward the user's teeth, thereby creating a visual fluorescent effect where plaque is present on the user's teeth

BRIEF DESCRIPTION OF THE DRAWINGS

FIG. 2A is a view similar to FIG. 2 showing a toothbrush head with surface mounted LEDs;

FIG. 3 is a side elevational view of a powered toothbrush in accordance with this invention;

FIG. 4 is a front elevational view of the toothbrush shown in FIG. 3.

FIG. 5 is a side elevational view of another embodiment of a manual toothbrush in accordance with this invention;

FIG. 6 is a front elevational view of the toothbrush shown in FIG. 5; and

FIG. 7 is a front elevational view of a powered toothbrush in accordance with this embodiment.

DETAILED DESCRIPTION

Figure 1:
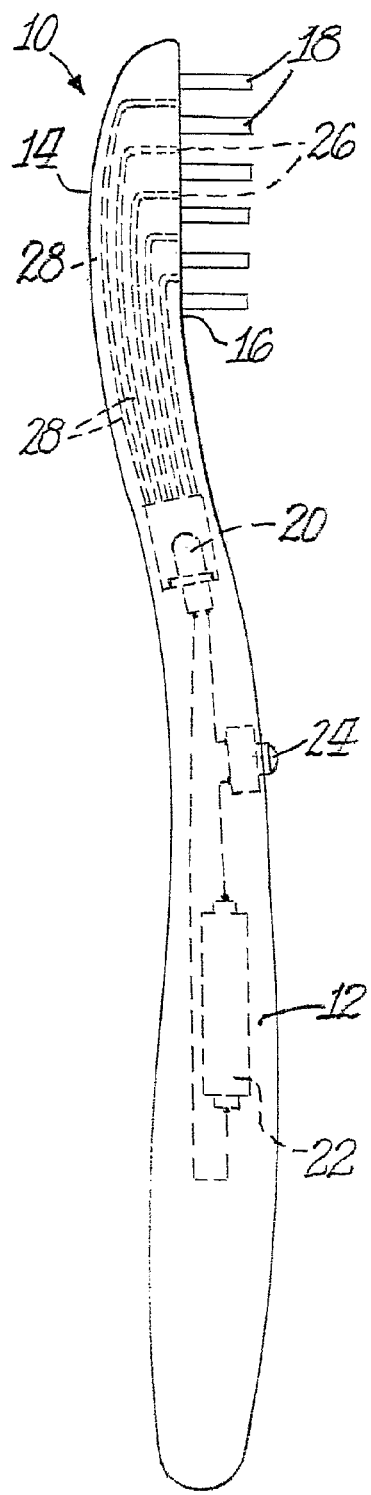
FIG. 1 is a side elevational view of one embodiment of a manual toothbrush in accordance with this invention.

FIGS. 1-4 show one embodiment and FIGS. 5-7 show another embodiment of a toothbrush that may used in accordance with this invention. In the first embodiment, toothbrush 10 includes a hollow handle 12 and a cleaning head 14. Cleaning head 14 has an outer surface 16 from which a plurality of cleaning elements 18 extend outwardly. Cleaning elements 18 may be of any suitable form such as bristles or elastomer members of any size or shape. The cleaning elements may also be a combination of different types of cleaning elements. The cleaning elements 18 are arranged on the outer surface 16 of the cleaning head to form a cleaning field. Thus the light(s) is located within the cleaning field.

Mounted within the hollow handle 12 is a source 20 of ultraviolet light. Any suitable source may be used such as miniature UV bulbs as manufactured by Welch Allyn.

Although miniature UV bulbs may be used this is a less preferred practice of the invention in that generally such bulbs are of relatively large size with high power consumption and tend to emit undesired UVB radiation. A more preferred practice of the invention, which is described in connection with the embodiment of FIGS. 5-7, is the use of LEDs 26A as the source 20 of ultraviolet light. A particular advantage of LEDs is that they can be surface mounted. In addition LEDs would have small or low power consumption and provide tight emissions in a tight spectrum band with minimum power requirements and have relatively low intensity. The LEDs could preferably have a safe UVA wavelength of 350-410 nm and more preferably a wavelength of 378-383 nm. Suitable LEDS can be obtained from Roithner Lasertechnik of Vienna, Austria. A suitable LED would be a 3.0.times.2.2.times.1.5 mn 3TOP LED. Whatever form of source is used, care should be taken to control the intensity of the UV radiation in order to avoid possible negative health effects.

Figure 2:
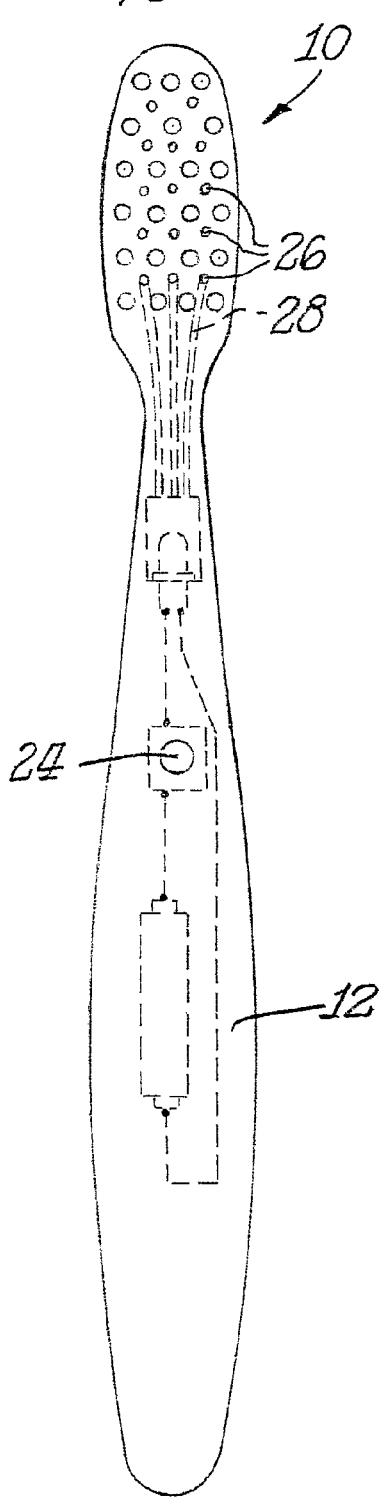
FIG. 2 is a front elevational view of the toothbrush shown in FIG. 1.

Although the ultraviolet light can constantly be emitted, it is preferable that the light source be selectively actuated. Any suitable structure could be used for accomplishing that task. FIGS. 1-2, for example, show the hollow handle 12 to include a battery 22 electrically connected to the UV light source 20, while FIGS. 5-7 show the hollow handle 12 to include a battery 22 electrically connected by suitable wiring 28A to the surface mounted LED devices 26A. A switch 24 located externally on the handle 12 selectively actuates the light source 20 (FIGS. 1, 2, 3, 4) or LEDs 26A.

When the light source 20 is actuated the light is transmitted from the handle to the carrier field and to at least one emitter 26 in the carrier field. The light could be transmitted in any suitable manner by transmitting structure 28 such as a light pipe, fiber optic, wiring 28A or other suitable devices. Preferably, the light(s) or emitters 26 are surface mounted and are located in the carrier field. FIGS. 2A and 5-7, for example, show two surface mounted emitters 26 in the form of LEDs 26A.

Although FIGS. 1-2 and 5-6 illustrate the toothbrush to be a manual toothbrush it is also possible to practice the invention with a powered toothbrush 10A and 10B as shown in FIGS. 3-4 and 7 respectively. In these embodiments powered toothbrush includes a moveable section 30 in the cleaning field. Movable section 30 could be of any size or shape and could be moved in any known manner such as continuous rotation in one direction, oscillating rotation or linear back and forth and/or side to side movement. One example of movement is an oscillating back and forth rotational movement such as disclosed in U.S. Pat. No. 5,625,916, all of the details of which are incorporated herein by reference thereto.

In the illustrated embodiment toothbrush 10A, 10B includes in its cleaning field a fixed portion 32 which does not move but which also contains cleaning elements. For the sake of simplicity the emitters 26 or LEDs 26A are located only in the fixed portion 32 rather than having to account for the movability of the optic fibers, light pipe or LED wiring if the emitters or LEDs were also located in the movable section 30. It is, however, in the scope of this invention that the emitters or LEDs could be in either the movable section 30 and/or the fixed section 32.

The invention could be practiced where the same switch 24 actuates both the light source 20 and the drive mechanism for the movable section 30. Alternatively, the movable section and the light source could be actuated by separate switches.

In one use of toothbrush 10, toothpaste would be applied to the outer ends of the cleaning elements 18, such as bristles. The toothpaste would incorporate a dye that has the characteristic of attaching itself to residual plaque on the tooth surface. The dye has the further characteristic that it can be actuated by the presence of ultraviolet radiation and would then have a fluorescent effect that would be easily visible to the user. In the normal use of the toothbrush the toothpaste would be applied to the teeth. The dye in the toothpaste would become attached to or be absorbed by residual plaque on the tooth surface. Upon rinsing the dye would be located only on the plaque. Either during or preferably immediately after the brushing and rinsing the user would actuate the ultraviolet light source through switch 24 to radiate the ultraviolet light from the emitters 26, 26A toward the teeth. If the dye becomes visible the user knows that not all of the plaque has been removed. If any residual plaque is present the dye would have remained attached to the plaque and in the presence of the ultraviolet radiation there would be readily visual fluorescent effect. This would alert the user that it is necessary to continue the brushing or to be at least aware that all of the plaque has not been removed. It would also provide immediate feedback to the user as to the user's brushing habits and areas where improvement in the brushing habits are necessary.

Any suitable dye could be used in the practice of this invention as long as the dye has the two characteristics noted above with respect to attaching itself to residual plaque and with respect to having a visible fluorescent effect in the presence of ultraviolet radiation. The dye should be absorbed in the plaque but not to the teeth. Before inspecting the teeth for plaque, the user would spit or rinse and spit the carrier and dye from the mouth, leaving only the dye attached to any plaque. One form of suitable dye is TINOPAL, marketed by Ciba Geigy. Preferably only a small amount of dye is necessary, such as 0.075 to 0.30% by volume of the total combination of the carrier and dye.

Various types of carriers may be used for applying the dye to the teeth. A convenient form of carrier could be by incorporating the dye in the toothpaste itself. Other forms of carriers could be conventional products that would be applied to the mouth. Such products include, but are not limited to, an oral rinse or mouthwash, a gum or lozenge, a polymer strip carrier which may or may not dissolve, or any other common means of delivering oral health benefits. For example, an oral rinse or mouthwash or other liquid applicator could be applied to the teeth and then the user discharges the applicator from the mouth, such as by a gargling with the liquid applicator or with water and then spitting the excess applicator and dye from the mouth leaving only the dye that is attached to the residual plaque in the mouth on the tooth surface. Preferably after the application the user would rinse with water to remove excess carrier and dye.

The UV light source whether from a toothbrush or a separate light source could then be actuated to radiate the UV light toward the teeth. In a broad practice of this invention, however, the ultraviolet or UV light source could be any device that provides the light emissions for the teeth. By using any of the combinations of applicator and UV light source the user can easily see how effective the cleaning operation, such as tooth brushing, has been.

In another use of the toothbrush of the present invention, toothpaste would be applied to the outer ends of the cleaning elements 18, such as bristles. The toothpaste would incorporate optical brighteners. In the normal use of the toothbrush the toothpaste would be applied to the teeth. The brighteners in the toothpaste would become attached to the tooth surface. Either during or immediately after the brushing the user would actuate the ultraviolet light source through switch 24 to radiate the ultraviolet light from the emitters 26, 26A toward the teeth. The brighteners in the presence of the ultraviolet radiation, would create a whitening effect.

The brightener has the characteristic that it can be actuated by the presence of ultraviolet radiation, such as that present in sunlight, and would then have a whitening or bleaching effect that would be easily visible to the user. In a preferred practice of this invention the ultraviolet radiation is emitted from a toothbrush; such that as a result, when the user is brushing the user's teeth there is an immediate, significant, visual whitening appearance. In a broad practice of this invention, however, the ultraviolet or UV light source could be any device that provides the light emissions for observing the teeth.

Various types of carriers may be used for applying the brightener to the teeth. The preferred form of carrier is incorporating the brightener in the toothpaste itself. As later described any suitable form of carrier may be used. The carrier would also include an adhering agent which would adhere to the teeth while the brighteners adhere to the adhering agent. As a result the brighteners remain on the outer surface of the teeth. A preferred adhering agent is a gantrez polymer, such as is used in antibacterial toothpastes to retain the antibacterial agent on the tooth surfaces. In the practice of this invention the optical brighteners could be selected from such types of brighteners which adhere to the whitening ingredients in such toothpastes and thereby the optical brighteners also remain on the teeth. Other forms of carriers could be conventional products that would be applied to the mouth. Such products include, but are not limited to, an oral rinse or mouthwash, a gum or lozenge, a polymer strip or any other common means of delivering oral health benefits. These carriers would also include some form of adhering agent which would deposit the brighteners on the surface of the teeth.

The presence of the optical brighteners on the teeth gives a white appearance when in the appearance of ultraviolet or fluorescent light. Such white appearance results when ultraviolet light or radiation is directed to the teeth such as by being incorporated in a toothbrush. The white appearance results from a combination of the bluish light from the radiation combining with any yellowness on the teeth to give a more white appearance. This same appearance would occur when the optical brighteners are in the presence of fluorescent lights in a room or in sunlight. The immediate creation of the whitening appearance would be beneficial in encouraging a user to have a regular brushing program so as to continue obtaining the whitening effect.

The benefit of incorporating the optical brighteners in toothpaste is that the optical brighteners would be applied through the brushing of one's teeth which would be reasonably easy and familiar to all users. If the optical brightener is incorporated in other forms of carriers the carriers should be such that the optical brighteners sufficiently adhere to the teeth to be present on the teeth and have the brightening effect when in the presence of ultraviolet energy. The activation of the brightener could thus occur through use of a special toothbrush as later described in which UV light is allowed to be transmitted through the bristle field of the toothbrush.

Any suitable optical brightener could be used in the practice of this invention. Suitable optical brighteners are common in the pulp and paper industry as well as being use in applications such as laundry detergent. Other uses of suitable optical brighteners are found in commercially available materials used to trace leaks in water systems. When these materials come into contact with ultraviolet radiation they have a whitening or bleaching effect. Typically, this chemical reaction occurs relatively quickly after the activation of the ultraviolet energy. One form of suitable brightener is TINOPAL, marketed by Ciba Geigy. Preferably only a small amount of brightener is necessary, such as 0.075 to 0.30% by volume of the total combination of the carrier and brightener.

In another use of toothbrush of the present invention, toothpaste would be applied to the outer ends of the cleaning elements 18, such as bristles. The toothpaste would incorporate oxidizing agents, such as hydrogen peroxide. In the normal use of the toothbrush the toothpaste would be applied to the teeth. Either during or immediately after the brushing the user would actuate the ultraviolet light source through switch 24 to radiate the ultraviolet light from the emitters 26, 26A toward the teeth. The oxidizing agent would be activated to speed the chemical process of whitening the stained teeth. Because of the short time required in practicing the invention the procedure could be repetitively performed and over time should result in an effective whitening action. This would have a benefit over conventional practices in being more convenient to use.

The above-mentioned process can be accomplished through the use of a toothbrush emitting light energy in the form of either ultraviolet radiation or infrared radiation. In the case of infrared energy heating would occur which would accelerate the process. The oxidizing agent could be applied to the teeth in any known manner and could be of any known composition, such as disclosed in the aforenoted patents and application of BriteSmile, Inc., all of the details of which are incorporated herein by reference thereto.

In a preferred practice of this invention the oxidizing agent is incorporated in a toothpaste composition. The invention, however, could also be practiced where the radiation is used to activate or accelerate reactions of specific formulations of whitening gels, whitening strips or other such products.

In contrast to the conventional practices of using various types of lamps the present invention utilizes, as shown in FIGS. 2A and 5-7, light energy preferably from LED devices 26A which can be very wavelength specific and much easier to physically place in the norms of typical toothbrush dimensions.

Unlike some previous applications the user, in the practice of this invention, would use the system more frequently for a very short usage period as opposed to the very long infrequent applications of the light energy as with prior techniques. Moreover, many applications in the past have required professional supervision. In contrast the present invention has the benefit of light energy that could be applied by the user in the user's home.

The benefit of incorporating the oxidizing agents in toothpaste is that the oxidizing agents would be applied through the brushing of one's teeth which would be reasonably easy and familiar to all users. The activation of the oxidizing agents could thus occur through use of a special toothbrush in which UW or infrared light is allowed to be transmitted through the bristle field of the toothbrush.

The toothbrush used in the practices of the invention could be a powered toothbrush type, i.e. a toothbrush in which there is movement of the bristles created by a motor and a drive transmission, or a manual toothbrush in which there is no driven movement of the bristles by a power source other than the user. The manual toothbrush could have the light source and the power supply for the light contained inside the brush handle with an external structure, such as a switch 24, for turning on the light. However, the tufts of bristles 18 would remain relatively stationary as is common in manual toothbrushes. Where the toothbrush is a powered toothbrush the light source or LEDs could be turned on or activated by the same switch which activates the power or could be turned on from a separate switch. The emitters or LEDs could be located in a movable section of the powered toothbrush or in a fixed section.

What is claimed is:

1. An oral care implement comprising:
   a handle;
   a head attached to said handle, said head having a front surface with cleaning elements extending outwardly therefrom;
   at least one light emitting diode located on said head to radiate light at a wavelength between 350-410 nm toward a user's teeth;
   wherein said at least one light emitting diode is surface mounted on the head so as to not protrude beyond the front surface of the head;
   wherein the at least one light emitting diode comprises a first one of the light emitting diodes and a second one of the light emitting diodes, each of the first and second ones of the light emitting diodes surface mounted on the head and aligned along a longitudinal axis of the head in a spaced-apart manner;
   wherein the first one of the light emitting diodes is directly surrounded by three bristle tufts and the second one of the light emitting diodes is directly surrounded by four bristle tufts;
   wherein each of the first and second ones of the light emitting diodes has a front surface that is flush with the front surface of the head, the front surface of the first and second ones of the light emitting diodes having a rectangular shape with four sides and four corners; and
   wherein two of the bristle tufts surrounding the first one of the light emitting diodes are positioned adjacent to one of the corners of the first one of the light emitting diodes, one of the bristle tufts surrounding the first one of the light emitting diodes is positioned adjacent to one of the sides of the first one of the light emitting diodes, and each of the bristle tufts surrounding the second one of the light emitting diodes is positioned adjacent to one of the corners of the second one of the light emitting diodes.

2. The oral care implement of claim 1 wherein no axis parallel to the longitudinal axis of the head intersects both of the first and second ones of the light emitting diodes and a cleaning element positioned axially between the first and second ones of the light emitting diodes.

3. The oral care implement of claim 1 wherein said oral care implement is a powered toothbrush having a movable section and a fixed section, and wherein the at least one light emitting diode is located on the head within said fixed section.

4. The oral care implement of claim 1 wherein said oral care implement is a powered toothbrush having a movable section and a fixed section, and wherein the at least one light emitting diode is located on the head within said movable section.

5. The oral care implement of claim 1 wherein said oral care implement is a powered toothbrush having a movable section, and wherein a single switch powers the powered toothbrush to move the movable section and activates the at least one light emitting diode.

6. The oral care implement of claim 1 wherein said oral care implement is a powered toothbrush having a movable section, and wherein a first switch powers the powered toothbrush to move the movable section and a second switch that is separate from the first switch activates the at least one light emitting diode.

7. An oral care implement comprising:
   a handle;
   a head attached to said handle, said head having a front surface with cleaning elements extending outwardly therefrom;
   at least one light emitting diode located on said head to radiate light at a wavelength between 350-410 nm toward a user's teeth;
   wherein the at least one light emitting diode comprises a first one of the light emitting diodes and a second one of the light emitting diodes, the first one of the light emitting diodes is directly surrounded by three bristle tufts and the second one of the light emitting diodes is directly surrounded by four bristle tufts;
   wherein each of the first and second ones of the light emitting diodes has a front surface that is flush with the front surface of the head, the front surface of the first and second ones of the light emitting diodes having a rectangular shape with four sides and four corners, and
   wherein two of the bristle tufts surrounding the first one of the light emitting diodes are positioned adjacent to one of the corners of the first one of the light emitting diodes, one of the bristle tufts surrounding the first one of the light emitting diodes is positioned adjacent to one of the sides of the first one of the light emitting diodes, and each of the bristle tufts surrounding the second one of the light emitting diodes is positioned adjacent to one of the corners of the second one of the light emitting diodes.

8. An oral care implement comprising:
a handle;
a head attached to said handle, said head having a front surface with cleaning elements extending outwardly therefrom;
at least one light emitting diode located on said head to radiate light at a wavelength between 350-410 nm toward a user's teeth;
wherein the at least one light emitting diode comprises a first one of the light emitting diodes and a second one of the light emitting diodes, each of the first and second ones of the light emitting diodes surface mounted on the head and aligned along a longitudinal axis of the head in a spaced-apart manner;
wherein the first one of the light emitting diodes is directly surrounded by three bristle tufts and the second one of the light emitting diodes is directly surrounded by four bristle tufts;
wherein each of the first and second ones of the light emitting diodes has a front surface, the front surface of the first and second ones of the light emitting diodes having a rectangular shape with four sides and four corners; and
wherein two of the bristle tufts surrounding the first one of the light emitting diodes are positioned adjacent to one of the corners of the first one of the light emitting diodes, one of the bristle tufts surrounding the first one of the light emitting diodes is positioned adjacent to one of the sides of the first one of the light emitting diodes, and each of the bristle tufts surrounding the second one of the light emitting diodes is positioned adjacent to one of the corners of the second one of the light emitting diodes.

* * * * *